(12) United States Patent
Won et al.

(10) Patent No.: US 8,420,755 B2
(45) Date of Patent: Apr. 16, 2013

(54) COMPOUNDS, CATALYST COMPOSITION COMPRISING THE SAME, AND METHOD FOR PREPARING OF CYCLOOLEFIN-BASED POLYMER USING THE SAME

(75) Inventors: Young-Chul Won, Daejeon (KR);
Sung-Ho Chun, Daejeon (KR);
Dai-Seung Choi, Daejeon (KR);
Dong-Woo Yoo, Daejeon (KR);
Bun-Yeoul Lee, Suwon-si (KR)

(73) Assignee: LG Chem, Ltd., Seoul (KR)

( * ) Notice: Subject to any disclaimer, the term of this patent is extended or adjusted under 35 U.S.C. 154(b) by 330 days.

(21) Appl. No.: 12/858,018

(22) Filed: Aug. 17, 2010

(65) Prior Publication Data

US 2011/0130532 A1 Jun. 2, 2011

(30) Foreign Application Priority Data

Aug. 18, 2009 (KR) .................. 10-2009-0076134
Aug. 11, 2010 (KR) .................. 10-2010-0077159

(51) Int. Cl.
| | |
|---|---|
| *C08F 4/52* | (2006.01) |
| *C08F 4/60* | (2006.01) |
| *C08F 32/00* | (2006.01) |
| *C07F 5/00* | (2006.01) |
| *C07F 9/02* | (2006.01) |

(52) U.S. Cl.
USPC ........... 526/134; 526/139; 526/145; 526/169;
526/169.1; 526/280; 526/281; 568/3; 568/2;
568/1; 568/10; 568/9; 568/8

(58) Field of Classification Search .................. 568/3, 2,
568/1, 10, 9, 8; 526/134, 139, 280
See application file for complete search history.

(56) References Cited

U.S. PATENT DOCUMENTS

| | | | |
|---|---|---|---|
| 3,330,815 A | 7/1967 | McKeon et al. | |
| 5,705,503 A | 1/1998 | Goodall et al. | |
| 6,124,231 A * | 9/2000 | Fritze et al. ................. | 502/152 |
| 6,177,376 B1 * | 1/2001 | Fritze et al. ................. | 502/110 |
| 6,455,650 B1 | 9/2002 | Lipian et al. | |

FOREIGN PATENT DOCUMENTS

| | | |
|---|---|---|
| EP | 0445755 A2 | 9/1991 |
| KR | 10-2002-0061625 A | 7/2002 |
| KR | 100843613 B1 * | 7/2003 |
| KR | 10-2007-0082909 A | 8/2007 |
| KR | 1020070082909 A * | 8/2007 |
| KR | 10-0843613 B1 | 7/2008 |
| WO | 2009/080174 A1 | 7/2009 |

OTHER PUBLICATIONS

Dureen, M.A.; Brown, C.C.; Stephan, D.W., Organometallics, 2010, 29, 6594-6607.*
Li et al., J. Am. Chem. Soc., 2002, 124, 12725-12741.*

(Continued)

*Primary Examiner* — Rip A. Lee
(74) *Attorney, Agent, or Firm* — Rothwell, Figg, Ernst & Manbeck, P.C.

(57) ABSTRACT

The present invention relates to a novel metallocene compound, a catalyst composition including the compound and an olefin polymer prepared using the same. The metallocene compound and the catalyst composition can be used for preparing the olefin polymer with high copolymerization degree and high molecular weight. Particularly, the block copolymer with high heat resistance can be prepared by using the metallocene compound, and the olefin polymer with high melting point (Tm) can be obtained, even if co-monomer is used at an increased amount in preparation of olefin polymer.

13 Claims, 1 Drawing Sheet

OTHER PUBLICATIONS

Abramo, G.P.; Li, L.; Marks, T.J., J. Am. Chem. Soc., 2002, 124, 13966-13967.*

International Search Report issued in PCT/KR2010/005267 on Apr. 26, 2011, 3 pages.

H. Li et al.: "Nuclearity and cooperativity effects in binuclear catalysts and cocatalysts for olefin polymerization," PNAS, vol. 103, No. 42, Oct. 17, 2006, pp. 15295-15302.

G. Welch et al.: "Thermal Rearrangement of Phosphine-B(C6F5)3 Adducts," Inorganic Chemistry, vol. 47, No. 6, 2008, pp. 1904-1906.

H. Li et al.: "Significant Proximity and Cocatalyst Effects in Binuclear Catalysis for Olefin Polymerization," Macromolecules, vol. 38, No. 22, 2005, pp. 9015-9027.

A. Motta et al.: "Proximity and Cooperativity Effects in Binuclear d0 Olefin Polymerization Catalysis. Theoretical Analysis of Structure and Reaction Mechanism," J. Am. Chem. Soc, vol. 131, No. 11, 2009, pp. 3974-3984.

* cited by examiner

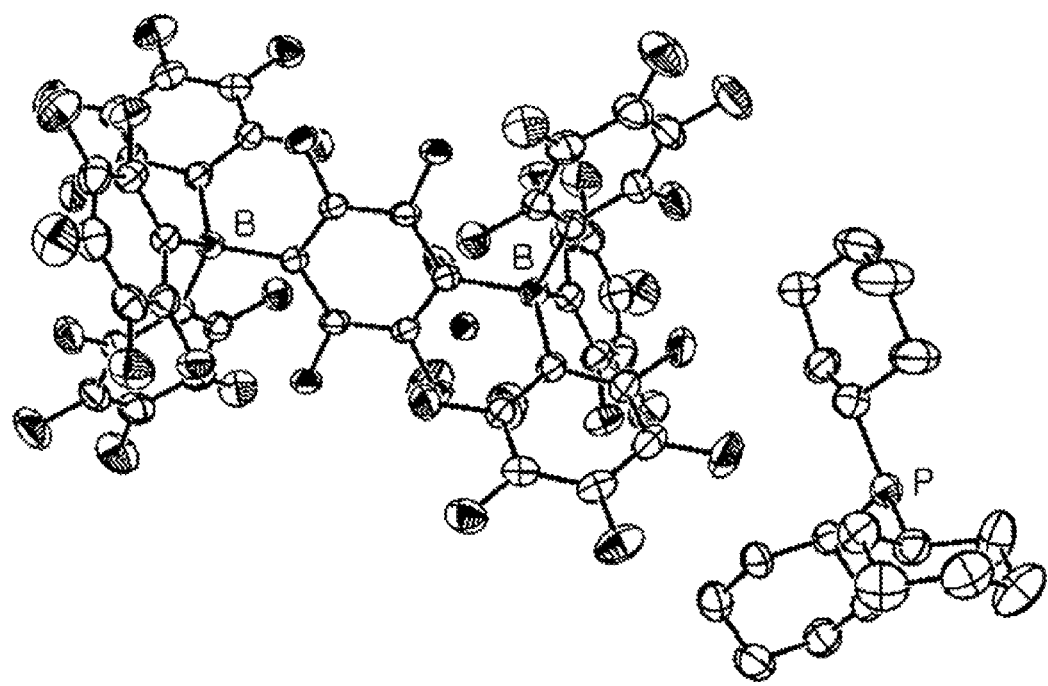

COMPOUNDS, CATALYST COMPOSITION COMPRISING THE SAME, AND METHOD FOR PREPARING OF CYCLOOLEFIN-BASED POLYMER USING THE SAME

TECHNICAL FIELD

The present invention relates to a novel compounds, a catalyst composition including the compound, and a method of preparing a cycloolefin-based polymer using the same.

This application claims priority to and the benefit of Korean Patent Application Nos. 10-2009-0076134 filed on Aug. 18, 2009 and 10-2010-0077159 filed on Aug. 11, 2010, which are hereby incorporated by reference for all purposes as if fully set forth herein.

BACKGROUND ART

Cycloolefin-based polymer is a polymer obtained by polymerizing cycloolefin-based monomer such as norbonene and has advantages in high transparency, heat resistance, a resistance to chemicals, but low birefringence and low absorption, compared to conventional olefin polymer. In considering that the norbonene-based resin can be a candidate material of substrate for flexible display due to its excellent optical property, the polymer needs a good adhesion to metal besides the heat resistance. That is, the polymer should have excellent adhesion to silicon, aluminum, copper, gold, silver, titanium, nickel and the like. Thus, a polar functional group has to be introduced to the polymer to improve the adhesive property.

When the cycloolefin-based monomer includes a polar group such as an ester group, the polar group increases a charge between molecules and adhesiveness to metal or other polymer, thereby being applied usefully for electronic material. Thus, the polymerization or copolymerization of norbonene including as ester group has been focused steadily (U.S. Pat. No. 3,330,815, EP0445755A2, U.S. Pat. No. 5,705,503, U.S. Pat. No. 6,455,650).

The catalyst having a complex structure must be used at an excessive amount of the catalyst to monomer of 1/100 to /1400 in the polymerization of norbonene including as ester group. Nevertheless, the polymerization yield was low and here was a difficult problem to remove the remnant catalyst.

The present inventor found that the catalyst having high activity for polymerization of cycloolefin-based polymer could be obtained by activating divalent palladium compound or zeo-valent palladium compound to phosphonium compound such as $[Cy_3P-H]^+[B(C_6P_5)_4]^-$ (KR10-0843613B). However, in case of some polar cycloolefins, the activity of catalyst is high at the low ratio of monomer/catalyst, but decreases sharply, if the ratio increased. This may be because that, as shown in reaction scheme 1, the propagation occurs when two metal centers acts simultaneously together. Namely, because the polar cycloolefin-based monomer has two ligands of an olefin group and a polar group to coordinate the metal, the propagation occurs by coordinating the olefin group with other metal after the polar group coordinates with on metal. If the polymerization proceeds according to the mechanism, polymerization rate is in inverse proportion to the square of the metal concentration. The activity of catalyst gets sensitive to the concentration of catalyst.

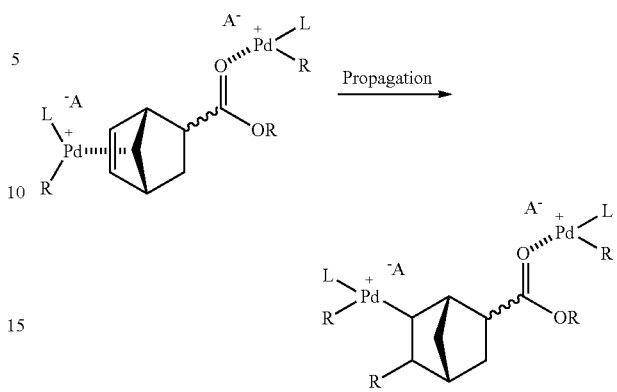

Reaction Scheme 1

Therefore, there is still a need for the compound having high catalytic activity in polymerization even at high ratio of monomer/catalyst.

DISCLOSURE

Technical Problem

To resolve the problems of prior art, the present invention provides a compound having high polymerizing activity even at high ratio of monomer/catalyst, and a method for polymerizing cycloolefin-based polymer.

Technical Solution

The present invention provides a compound represented by Chemical formula 1:

$$\{[H-P(R1)_3]^+\}_2[(C_6F_5)_3B-Z-B(C_6F_5)_3]^{2-} \quad \text{Chemical formula 1}$$

in Chemical formula 1,

R1 is the same or different from each other and is independently selected from the group consisting of hydrogen, a linear or branched C1-C20 alkyl group, a substituted or unsubstituted C3-C12 cycloalkyl group, a substituted or unsubstituted C6-C40 aryl group, a substituted or unsubstituted C7-C15 aralkyl group, a substituted or unsubstituted C7-C15 aralkenyl, and a substituted or unsubstituted C2-C20 alkynyl group;

Z is a group connecting two boron atoms by a covalent bond, which is selected from the group consisting of a linear or branched C1-C20 alkylene group, a substituted or unsubstituted C3-C12 cycloalkylene group, a substituted or unsubstituted C6-C40 arylene group, a substituted or unsubstituted C7-C15 aralkylene group, a substituted or unsubstituted C2-C20 alkenylene group, and C2-C20 alkylene group.

In addition, the present invention provides a catalyst composition comprising the compound.

Further, the present invention provides a method for preparing a cycloolefin-based polymer using the catalyst composition.

Advantage Effect

According the present invention, two cationic metal centers can be positioned closely each other regardless of the concentration of metal compound, by using the compound including two anions in a molecule as a co-catalyst, thereby providing a high activity even at the high ratio of [monomer]/[catalyst] in the polymerization process for a polar cycloolefin-based monomer.

DESCRIPTION OF DRAWINGS

FIG. 1 is an analysis result of single-crystal X-ray diffraction of the compound according to Example 1.

MODE FOR INVENTION

Hereinafter, the embodiments of the present invention will be described in more details.

In Chemical formula 1, each functional group can be substituted with halogen, cyano group, or phenylsulfonyl, but not limited thereto.

In Chemical formula 1, R1 is cyclohexyl, and Z is —$C_6F_4$— preferably, but R1 and Z are not limited thereto.

The compound represented by Chemical formula 1 can be preferably used as a co-catalyst for preparation of a cycloolefin-based polymer.

When Group 10 metals such as palladium as a precatalyst are activated by using the compound represented by Chemical formula 1, two palladium centers can be positioned closely regardless of the concentration of catalyst. Therefore, even if the concentration of catalyst is low, two palladium centers are positioned closely and shows high polymerization activity at low ratio of [monomer]/[catalyst] (reaction scheme 2).

Reaction scheme 2

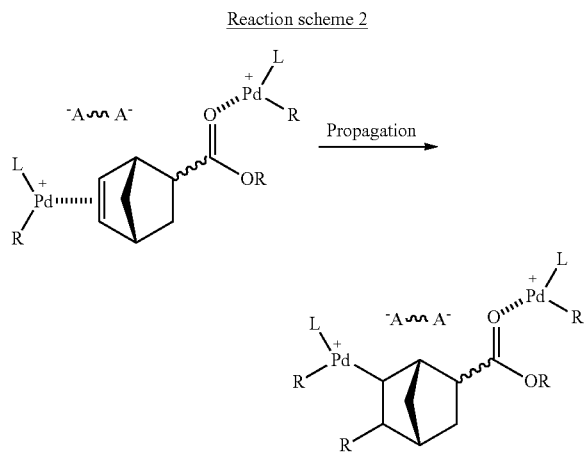

The polymerization of the norbonene monomer including the polar group occurs, when the olefin group with other metal after the polar group coordinates with one metal. In case that the conventional co-catalyst is used for polymerizing the norbonene monomer including the polar group, and the other metal catalyst has low chance of coordinating double bond after one metal catalyst coordinate with the polar group, at low concentration of catalyst in a polymerization solution. However, in case that the compound of Chemical formula 1 according to the present invention is used as co-catalyst, two metal centers are always closely each other, resulting in making the other metal catalyst easily coordinating with double bond after one metal catalyst coordinates with the polar group. Therefore, the present invention can provide a catalyst having a high polymerizing activity for cycloolefin-based monomer including the polar group, even at low concentration of catalyst.

The preparation of compound represented by Chemical formula 1 can be described in the following part in more detail.

In addition, the present invention provides a catalyst composition comprising the compound.

Preferably, the catalyst composition comprises a precatalyst of Group 10 metal compound represented by Chemical formula 2 and a co-catalyst of a compound represented by Chemical formula 1:

$$[M_a(R)_b(L_1)_c]$$ Chemical formula 2

In Chemical formula 2,
M is Group 10 metal;
R is a hydrocarbyl ligand;
$L_1$ is a neutral ligand; and
a is 1 or 2, b is 0 or 2, c is 0 or 3, provided that a, b and c satisfy the formulae of $0<b++c\leq3$ and $3\leq a+b+c\leq5$.

In Chemical formula 2, R is preferably represented by Chemical formula 3:

Chemical formula 3

In Chemical formula 3,
X and Y are independently a hetero atom selected from the group consisting of S, O and N;
the hetero atom may be linked to hydrogen, a linear or branched C1-C20 alkyl, C1-C20 alkenyl, C1-C20 vinyl, C5-C12 cycloalkyl which is unsubstituted or substituted with a hydrocarbon, C6-40 aryl group which is unsubstituted or substituted with a hydrocarbon, C7-15 aralkyl group which is unsubstituted or substituted with a hydrocarbon, or C3-C20 alkynyl;
R* is selected from the group consisting of a linear or branched C1-C20 alkyl, C1-C20 alkenyl, C1-C20 vinyl, C5-C12 cycloalkyl which is unsubstituted or substituted with a hydrocarbon, C6-40 aryl which is unsubstituted or substituted with a hydrocarbon, C7-15 aralkyl group which is unsubstituted or substituted with a hydrocarbon, and C3-C20 alkynyl(alkynyl).

In Chemical formula 2, $L_1$ is preferably represented by Chemical formula 4:

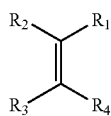

Chemical formula 4 in Chemical formula 4,
$R_1$, $R_2$, $R_3$ and $R_4$ are the same or different from each other and are independently selected from the group consisting of hydrogen; halogen; a linear or branched C1-C20 alkyl which is unsubstituted or substituted with a halogen; a linear or branched C2-C20 alkenyl which is unsubstituted or substituted with a halogen; a linear or branched C3-C20 alkynyl which is unsubstituted or substituted with a halogen; C3-C12 cycloalkyl which is unsubstituted or substituted with alkyl, alkenyl, alkynyl, halogen, haloalkyl, haloalkenyl, or haloalkynyl; C6-C40 aryl which is unsubstituted or substituted with alkyl, alkenyl, alkynyl, halogen, haloalkyl, haloalkenyl, or haloalkynyl; C7-C15 aralkyl which is unsubstituted or substituted with alkyl, alkenyl, alkynyl, halogen, haloalkyl, haloalkenyl, or haloalkynyl; and a non-hydrocarbonaceous polar group including at least an atom selected from the group consisting of oxygen, nitrogen, phosphorus, sulfur, silicon and boron, the non-hydrocarbonaceous polar group is —$R_9OR_9'$, —$OR_9'$, —$OC(O)OR_9'$, —$R_9OC(O)OR_9'$, —$C(O)R_9'$, —$R_9C(O)OR_9'$, —$C(O)OR_9'$, —$R_9C(O)R_9'$, —$OC(O)R_9'$, —$R_9OC(O)R_9'$, —$(R_9O)_k$—$OR_9'$, —$(OR_9)_k$—$OR_9'$, —$C(O)$—$O$—$C(O)R_9'$, or —$R_9C(O)$—$O$—$C(O)R_9'$, each $R_9$ is a linear or branched C1-C20 alkylene which is unsubstituted or substituted with a halogen; a linear or branched C2-C20 alkenylene which is unsubstituted or substituted with a halogen; a linear or branched C3-C20 alkynylene which is unsubstituted or substituted with a halogen; a C3-C12 cycloalkylene which is unsubstituted or substituted with alkyl, alkenyl, alkynyl, halogen, haloalkyl, haloalkenyl, or haloalkynyl; C6-C40 arylene which is unsubstituted or substituted with alkyl, alkenyl, alkynyl, halogen, haloalkyl, haloalkenyl, or haloalkynyl; or C7-C15 aralkylene which is unsubstituted or substituted with alkyl, alkenyl, alkynyl, halogen, haloalkyl, haloalkenyl, or haloalkynyl, each $R_9'$ is selected from the group consisting of hydrogen; halogen; a linear or branched C1-C20 alkyl which is unsubstituted or substituted with a halogen; a linear or branched C2-C20 alkenyl which is unsubstituted or substituted with a halogen; a linear or branched C3-C20 alkynyl which is unsubstituted or substituted with a halogen; C3-C12 cycloalkyl which is unsubstituted or substituted with alkyl, alkenyl, alkynyl, halogen, haloalkyl, haloalkenyl, or haloalkynyl; C6-C40 aryl which is unsubstituted or substituted with alkyl, alkenyl, alkynyl, halogen, haloalkyl, haloalkenyl, or haloalkynyl; C7-C15 aralkyl which is unsubstituted or substituted with alkyl, alkenyl, alkynyl, halogen, haloalkyl, haloalkenyl, or haloalkynyl; alkoxy; haloalkoxy; carbonyloxy; and halocarbonyloxy; and k is an integer of 1 to 10.

In Chemical formula 4, while not particularly limited, at least one of $R_1$, $R_2$, $R_3$ and $R_4$ is preferably a polar group.

In Chemical formula 2, M is preferably palladium, but not limited thereto.

In the catalyst composition, the compound represented by Chemical formula 2 is preferably tris(dibenzylideneacetone)dipalladium(0)($Pd_2(dba)_3$) or palladiumacetate($Pd(OAc)_2$).

In the catalyst composition, the molar ratio of the compound represented by Chemical formula 1: the compound represented by Chemical formula 2 is 1:2 preferably, but not limited thereto.

In addition, the present invention provides a method for preparing a cycloolefin-based polymer using the catalyst composition.

The cycloolefin-based monomer to prepare the cycloolefin-based polymer is represented by Chemical formula 5:

Chemical formula 5

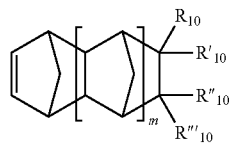

in Chemical formula 5, m is an integer of 0 to 4;

$R_{10}$, $R'_{10}$, $R''_{10}$ and $R'''_{10}$ are the same or different from each other, and are independently selected from the group consisting of hydrogen; halogen; a linear or branched C1-C20 alkyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; C3-12 cycloalkyl group which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-40 aryl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a polar functional group including at least an atom selected from the group of oxygen, nitrogen, phosphor, sulfur, silicone and boron atom, $R_{10}$ and $R'_{10}$, or $R''_{10}$ and $R'''_{10}$ may be linked each other to form C1-C10 alkylidene group, or one of $R_{10}$ and $R'_{10}$ may be linked to one of $R''_{10}$ and $R'''_{10}$ to form a unsaturated or saturated C4-C12 alicyclic ring, or a C6-C24 aromatic ring, the polar group is selected from the group of —$R_5OR_6$, —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$—, —$R_5C(=S)SR_6$, —$R_5SO_3R_6$, —$SO_3R_6$, —$R_5N=C=S$, —$N=C=S$, —NCO, —$R_5$—NCO, —CN, —$R_5CN$, —$NNC(=S)R_6$, —$R_5NNC(=S)R_6$, —$NO_2$, —$R_5NO_2$,

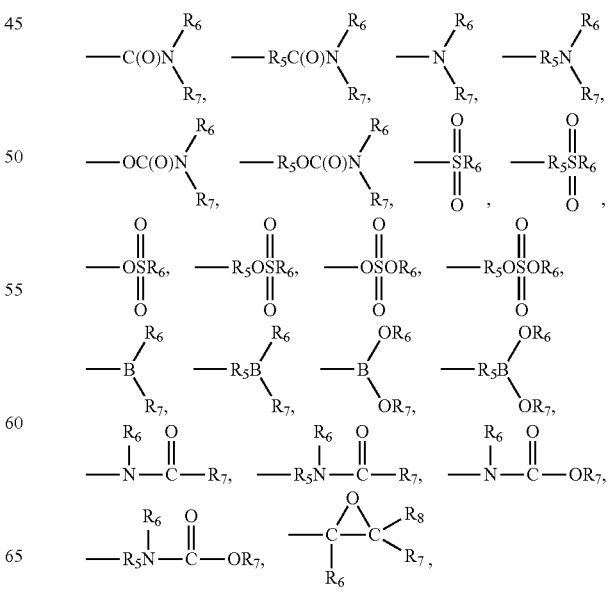

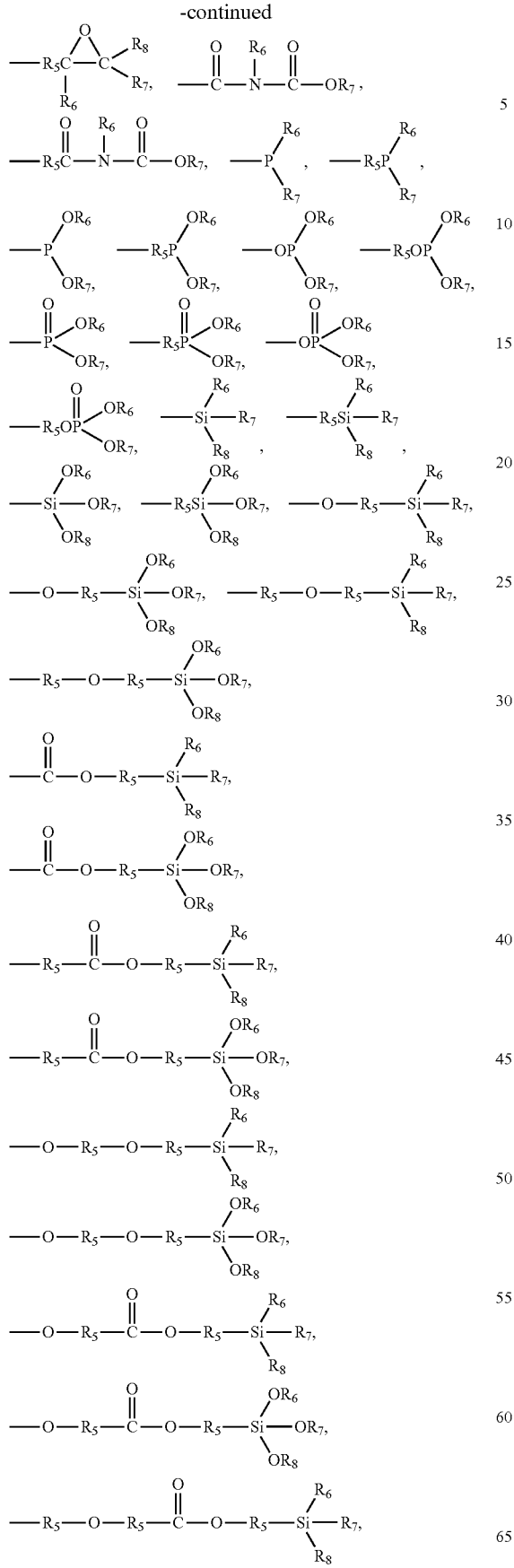
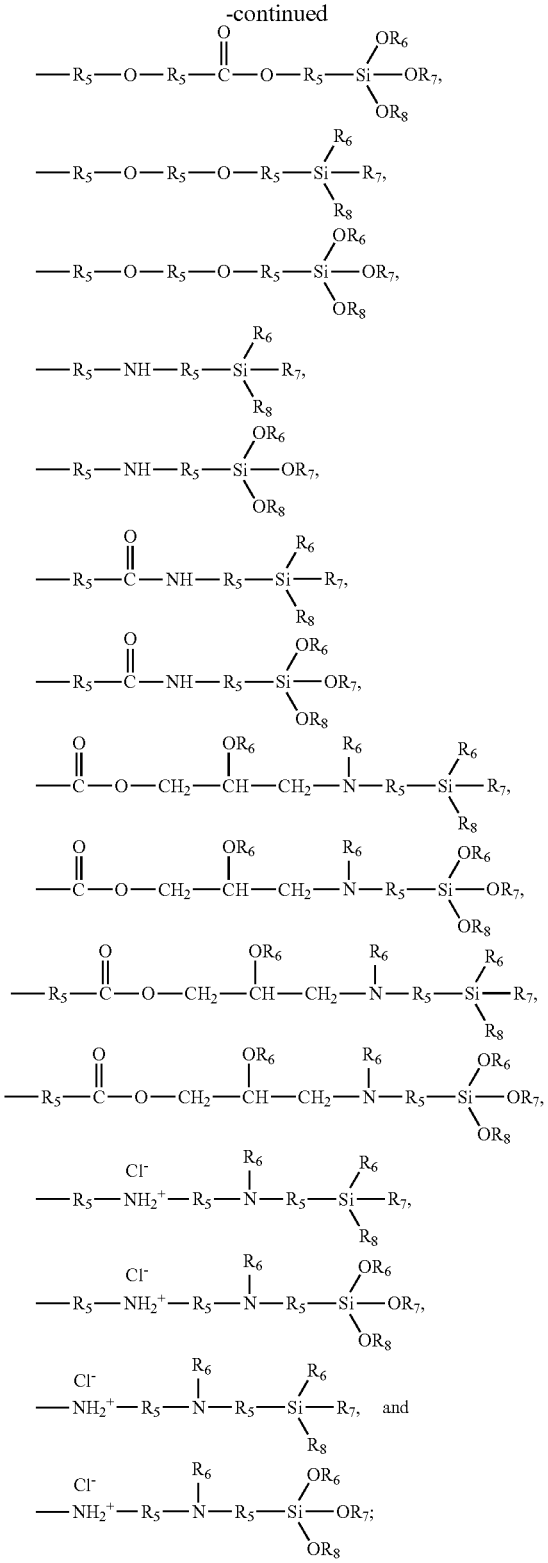
in the polar group,
$R_5$ is the same or different from each other and is independently a linear or branched C1-C20 alkylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C3-C12 cycloalkylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-C40 arylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C1 to C20 alkoxylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a C1 to C20 carbonyloxylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy, $R_6$, $R_7$ and $R_8$ are the same or different from each other and are independently selected from the group consisting of hydrogen; halogen; a linear or branched C1-C20 alkyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C3-12 cycloalkyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-40 aryl group which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C1-C20 alkoxy which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a C1-C20 carbonyloxy which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy, and p is an integer of 1 to 10.

In the method of preparing the cycloolefin-based polymer, while not particularly limited, the cycloolefin-based monomer represented by Chemical formula 5 wherein, at least one of $R_{10}$, $R'_{10}$, $R''_{10}$ and $R'''_{10}$. is a polar group is preferably used.

In Chemical formula 5, the polar group is preferably —$CO_2R$, —$C(O)NR_2$, —$C(O)N(R)C(O)R$, —$N(R)C(O)R$, —$OC(O)OR$, —$C(O)R$, —$OC(O)R$, —$OSO_3R$, or —$OS(O)_2R$, where R is hydrogen, or acyclic or cyclic C1-C10 alkyl.

More preferably, the cycloolefin-based monomer represented by Chemical formula 5 is 5-norbonene-2-carboxylic acid.

In the method for preparing cycloolefin-based polymer of the present invention, the cycloolefin-based monomer can contain 0.1 to 99.9 mol % of cycloolefin-based monomer having a polar group, and the cycloolefin-based monomer having polar group can contains endo-isomer, exo-isomer, and a mixture thereof, but the mixing ratio is not limited particularly.

Further, in the method for preparing cycloolefin-based polymer, when the cycloolefin-based monomer is a cycloolefin-based monomer having a polar group, the monomer can contain cycloolefin-based co-monomer not having a polar group.

Also, the cycloolefin-based polymer is a homopolymer of cycloolefin-based monomer, a two-membered copolymer or three-membered copolymer prepared from cycloolefin-based monomers including different polar groups each other, or a two-membered copolymer or three-membered copolymer prepared from a cycloolefin-based monomer including a polar group and a cycloolefin-based monomer not including a polar group.

In the method for preparing cycloolefin-based polymer, the molar ratio of cycloolefin-based monomer/Group 10 metal such as palladium is preferably 5,000 to 100,000 but not limited thereto.

A solvent can be used in preparation of cycloolefin-based polymer. The solvent cannot be limited particularly, but is preferably dichloromethane, dichloroethane, toluene, chlorobenzene, and etc. The weight ratio of solvent to cycloolefin-based monomer is in the range of 0.5:1 to 5:1. If the ratio is excessively low, there is a problem to agitate in the polymerizing reaction due to high viscosity of solution.

In the method for preparing cycloolefin-based polymer, the pressure in polymerizing process is 1 bar and the temperature is 0 to 100° C., and preferably 80 to 100° C., but the pressure and temperature cannot be limited thereto.

The cycloolefin-based polymer prepared in accordance with the present invention, shows high molecular weight, and more specifically a weight average molecular weight of 300,000 or higher, compared with that of polymer prepared by suing the conventional catalyst system.

EXAMPLES

The present invention is further explained in more detail with reference to the following examples. These examples, however, should not be interpreted as limiting the scope of the present invention in any manner.

Preparation Example 1

Synthesis of $\{[H\text{—}PCy_3]^+\}_2[(C_6P_5)_3B\text{—}C_6F_4\text{—}B[(C_6F_5)_3]^{2-}$ The titled compound was synthesized as shown in reaction scheme 3, where Cy means cyclohexyl group.

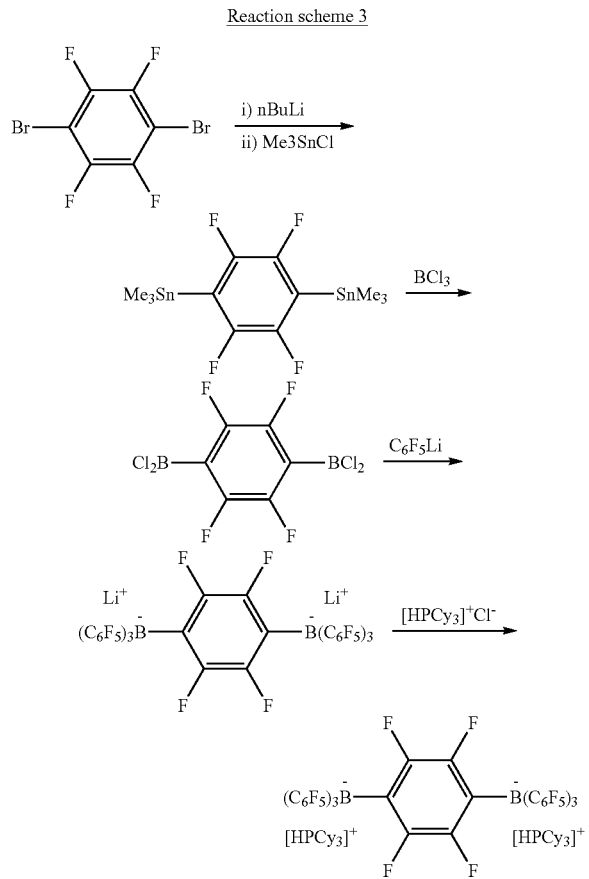

Reaction scheme 3

1) Preparation of $Me_3Sn(C_6F_4)SnMe_3$ 1.50 g (0.01 mole) of 2,3,5,6-tetrafluorodibromobenzene was put to 250 mL flask with one neck and round bottom in dry ice box to remove the moisture, and then dissolved in 70 mL of dehydrated tetrahydrofuran. Then, 8.5 mL (0.02 mole) of n-butyl lithium was taken with syringe and, added dropwisely in dry ice acetone bath at −78° C., and agitated for 40 minutes. 3.90 g (0.02 mole) of trimethyltinchloride was dissolved in 30 mL of tetrahydrofuran and added slowly to the agitating flask. The reaction mixture was agitated at −78° C. for 2 hours, and then, agitated additionally at room temperature for 20 hours. The reaction was quenched with addition of HCl (100 mL 0.1M aqueous solution) at room temperature, and only organic layer was extracted. The moisture of the extracted product was removed with Magnesium sulfate, and then, the solvent was removed under vacuum. 2.76 g of the white product was sublimated under the condition of 80° C./0.01 mmHg to obtain the solid product, $Me_3Sn(C_6F_4)SnMe_3$.

2) Preparation of $Cl_2B(C_6F_4)BCl_2$ 1.50 g (0.003 mole, Me means methyl) of $Me_3Sn(C_6F_4)SnMe_3$ was added to 100 mL flask being capable of sealable connector, and the flask was connected to dual manifold vacuum line via connector. Then, 3 mL of trichloroborane gas was added to flask via nitrogen line. After reacting for 14 days, the remaining trichloroborane gas was removed under vacuum. The produced compound was dissolved in pentane in dry ice box, filter with glass filter, and the solvent was removed by vacuum pump to produce solid product, $Cl_2B(C_6F_4)BCl_2$.

3) Preparation of $[Li^+]_2[(C_6F_5)_3B\text{—}C_6F_4\text{—}B[(C_6F_5)_3]^{2-}$ 1.53 mL (0.0123 mole) of $C_6F_5Br$ was put in toluene in 50 omL flask. Then, 7.67 mL (0.0123 mole) of n-butyl lithium was taken with syringe and, added dropwisely in dry ice acetone bath at −78° C., and agitated for 2 hours to obtain $C_6F_5Li$. 0.64 g (0.002 mole) of $Cl_2B(C_6F_4)BCl_2$ was dissolved in 40 mL of toluene, added slowly to the agitating flask at −78° C. with syringe, and the reaction was performed continuously for 12 hours by elevating the temperature to the room temperature. The remaining solvent was removed under vacuum to produce salts of $(Li^+)_2[(C_6F_5)_3B\text{—}C_6F_4\text{—}B[(C_6F_5)_3]^{2-}$.

4) Preparation of $\{[H\text{—}PCy_3]^+\}_2[(C_6F_5)_3B\text{—}C_6F_4\text{—}B[(C_6F_5)_3]^{2-}$ 0.42 g (0.00035 mole) of $[Li^+]_2[(C_6F_5)_3B\text{—}C_6F_4\text{—}B[(C_6F_5)_3]_{2-}$ was put to 250 mL flask with one neck and round bottom, and then dissolved in 50 mL of dichlromethan. Then, 0.22 g (0.0007 mole) of $Cy_3PHCl$ was added to the flask where $[Li^+]_2[(C_6F_5)_3B\text{—}C_6F_4\text{—}B[(C_6F_5)_3]^2$ and agitated for 10 minutes to identify white precipitate presumed to LiCl. The reaction mixture was filtered with glass filter and the solvent was removed under vacuum to produce $[(H\text{—}PCy_3)]^+_2[(C_6F_5)_3B\text{—}C_6F_4\text{—}B[(C_6F_5)_3]^{2-}$.

FIG. 1 is an analysis result of single-crystal X-ray diffraction of the compound according to Example 1.

Preparation Example 2

Synthesis of $\{[H\text{—}PPh_3]^+\}_2[(C_6F_5)_3B\text{—}C_6F_4\text{—}B[(C_6F_5)_3]^{2-}$ The method was performed as the same method of Preparation Example 1, except for use of $PPh_3PHCl$ instead of $Cy_3PHCl$.

Preparation Example 3

Synthesis of $\{[H\text{—}P(t\text{-}Bu)_3]^+\}_2[(C_6F_5)_3B\text{—}C_6F_4\text{—}B[(C_6F_5)_3]^{2-}$ The method was performed as the same method of Preparation Example 1, except for use of $t\text{-}Bu_3PHCl$ instead of $Cy_3PHCl$.

Example 1

Polymerization 1.0 mg (0.001 mmol) of $Pd_2(dba)_3$ and 1.9 mg (0.001 mmol) of $\{[H\text{—}PCy_3]^+\}_2[(C_6F_5)_3B\text{—}C_6F_4\text{—}B(C_6F_5)_3]^{2-}$ (Cy means cyclohexyl) as a co-catalyst were put to flask in dry ice box, and was dissolved with addition of 3.32 g (21.8 mmol, [monomer]/[Pd]=11,000) of 5-norbonene-2-carboxylic acid methyl ester and 10 g of dichloroethane. The reaction was performed at 90° C. for 24 hours, cooled to room temperature, and then precipitated with methanol to collect the product by filtering. The collected product was dried at 60° C. with vacuum pump to obtain 2.7 g of white solid (yield: 81%). Weight average molecular weight (Mw) of the product was 546,700 and Mw/Mn was 2.32.

Example 2

Polymerization

This Example was performed as the same method of Example 1, except that Pd(OAc)$_2$ was used as a catalyst at the same mole of Pd$_2$(dba)$_3$, instead of Pd$_2$(dba)$_3$. The yield was 2.1 g (63%), Mw was 850,100, and Mw/Mn was 2.52.

Example 3

Polymerization

This Example was performed as the same method of Example 1, except that the same weight of toluene was used instead of dichloroethane. As a result, The yield was 2.5 g (75%), Mw was 506,030, and Mw/Mn was 22.27.

Comparative Example 1

Polymerization using [HPCy$_3$]$^+$[B(C$_6$F$_5$)$_4$]$^-$ as a co-catalyst 1.0 mg (0.0010 mmol) of Pd$_2$(dba)$_3$ and 2.1 mg (0.002 mmol) of HPCy$_3$B(C$_6$F$_5$)$_4$ (Cy means cyclohexyl) as a co-catalyst were put to flask in dry ice box, and was dissolved with addition of 3.32 g (21.8 mmol) of 5-norbonene-2-carboxylic acid methyl ester and 10 g of toluene. The reaction was performed at 90° C. for 24 hours, cooled to room temperature, and then precipitated with methanol to collect the product by filtering. The collected product was dried at 60° C. with vacuum pump to obtain 1.4 g of white solid (yield: 42%). Weight average molecular weight (Mw) of the product was 232,200 and Mw/Mn was 2.41.

The invention claimed is:

1. A compound represented by Chemical formula 1:

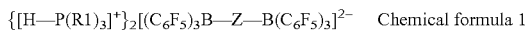  Chemical formula 1 wherein,
R1 is the same or different from each other and is independently selected from the group consisting of hydrogen, a linear or branched C1-C20 alkyl group, a substituted or unsubstituted C3-C12 cycloalkyl group, a substituted or unsubstituted C6-C40 aryl group, a substituted or unsubstituted C7-C15 aralkyl group, a substituted or unsubstituted C7-C15 aralkenyl, and a substituted or unsubstituted C2-C20 alkynyl group;
Z is a group connecting two boron atoms by a covalent bond, which is selected from the group consisting of a linear or branched C1-C20 alkylene group, a substituted or unsubstituted C3-C12 cycloalkylene group, a substituted or unsubstituted C6-C40 arylene group, a substituted or unsubstituted C7-C15 aralkylene group, a substituted or unsubstituted C2-C20 alkenylene group, and C2-C20 alkylene group.

2. The compound of claim 1, wherein the R1 in Chemical Formula 1 is cyclohexyl, and Z is —C$_6$F$_4$—.

3. A catalyst composition comprising a precatalyst of Group 10 metal compounds represented by Chemical formula 2 and a co-catalyst of a compound represented by Chemical formula 1:

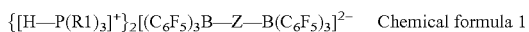  Chemical formula 1 wherein,
R1 is the same or different from each other and is independently selected from the group consisting of hydrogen, a linear or branched C1-C20 alkyl group, a substituted or unsubstituted C3-12 cycloalkyl group, a substituted or unsubstituted C6-40 aryl group, a substituted or unsubstituted C7-15 aralkyl group, a substituted or unsubstituted C7-C15 aralkyl, a substituted or unsubstituted C7-C15 aralkenyl, and a substituted or unsubstituted C2-C20 alkynyl group; and
Z is a group connecting two boron atoms by a covalent bond, which is selected from the group consisting of a linear or branched C1-C20 alkylene group, a substituted or unsubstituted C3-C12 cycloalkylene group, a substituted or unsubstituted C6-C40 arylene group, a substituted or unsubstituted C7-C15 aralkylene group, a substituted or unsubstituted C2-C20 alkenylene group, and C2-C20 alkylene group;

$[M_a(R)_b(L_1)_c]$  Chemical formula 2 wherein,
M is Group 10 metal;
R is a hydrocarbyl ligand;
L$_1$ is a neutral ligand; and
a is 1 or 2, b is 0 or 2, c is 0 or 3, with proviso that a, b and c satisfy the formulae of $0<b+c\leq3$ and $3\leq a+b+c\leq5$.

4. The catalyst composition of claim 3, wherein R of Chemical formula 2 is represented by Chemical formula 3:

  Chemical formula 3 wherein,
X and Y are independently a hetero atom selected from the group consisting of S, O and N;
the hetero atom may be linked to hydrogen, a linear or branched C1-C20 alkyl, C2-C20 alkenyl, vinyl, C5-C12 cycloalkyl which is unsubstituted or substituted with a hydrocarbon, C6-40 aryl group which is unsubstituted or substituted with a hydrocarbon, C7-15 aralkyl group which is unsubstituted or substituted with a hydrocarbon, or C3-C20 alkynyl; and
R* is selected from the group consisting of a linear or branched C1-C20 alkyl, C2-C20 alkenyl, vinyl, C5-C12 cycloalkyl which is unsubstituted or substituted with a hydrocarbon, C6-40 aryl which is unsubstituted or substituted with a hydrocarbon, C7-15 aralkyl group which is unsubstituted or substituted with a hydrocarbon, and C3-C20 alkynyl.

5. The catalyst composition of claim 3, wherein L$_1$ of Chemical formula 2 is represented by Chemical formula 4:

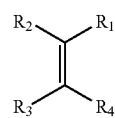  Chemical formula 4 wherein,
R$_1$, R$_2$, R$_3$ and R$_4$ are the same or different from each other and are independently selected from the group consisting of hydrogen; halogen; a linear or branched C1-C20 alkyl which is unsubstituted or substituted with a halogen; a linear or branched C2-C20 alkenyl which is unsubstituted or substituted with a halogen; a linear or branched C3-C20 alkynyl which is unsubstituted or substituted with a halogen; C3-C12 cycloalkyl which is unsubstituted or substituted with alkyl, alkenyl, alkynyl, halogen, haloalkyl, haloalkenyl, or haloalkynyl; C6-C40 aryl which is unsubstituted or substituted with alkyl, alkenyl, alkynyl, halogen, haloalkyl, haloalkenyl, or haloalkynyl; C7-C15 aralkyl which is unsubstituted or substituted with alkyl, alkenyl, alkynyl, halogen, haloalkyl, haloalkenyl, or haloalkynyl; and a non-hydrocarbonaceous polar group including at least an atom selected from the group consisting of oxygen, nitrogen, phosphorus, sulfur, silicon and boron, the non-hydrocarbonaceous polar group is —$R_9OR_9'$, —$OR_9'$, —$OC(O)OR_9'$, —$R_9OC(O)OR_9'$, —$C(O)R_9'$, —$R_9C(O)OR_9'$, —$C(O)OR_9'$, —$R_9C(O)R_9'$, —$OC(O)R_9'$, —$R_9OC(O)R_9'$, —$(R_9O)_k$—$OR_9'$, —$(OR_9)_k$—$OR_9'$, —$C(O)$—$O$—$C(O)R_9'$, or —$R_9C(O)$—$O$—$C(O)R_9'$, each $R_9$ is a linear or branched C1-20 alkylene which is unsubstituted or substituted with a halogen; a linear or branched C2-C20 alkenylene which is unsubstituted or substituted with a halogen; a linear or branched C3-C20 alkynylene which is unsubstituted or substituted with a halogen; a C3-C12 cycloalkylene which is unsubstituted or substituted with alkyl, alkenyl, alkynyl, halogen, haloalkyl, haloalkenyl, or haloalkynyl; C6-C40 arylene which is unsubstituted or substituted with alkyl, alkenyl, alkynyl, halogen, haloalkyl, haloalkenyl, or haloalkynyl; or C7-C15 aralkylene which is unsubstituted or substituted with alkyl, alkenyl, alkynyl, halogen, haloalkyl, haloalkenyl, or haloalkynyl, each $R_9'$ is selected from the group consisting of hydrogen; halogen; a linear or branched C1-C20 alkyl which is unsubstituted or substituted with a halogen; a linear or branched C2-C20 alkenyl which is unsubstituted or substituted with a halogen; a linear or branched C3-C20 alkynyl which is unsubstituted or substituted with a halogen; C3-C12 cycloalkyl which is unsubstituted or substituted with alkyl, alkenyl, alkynyl, halogen, haloalkyl, haloalkenyl, or haloalkynyl; C6-C40 aryl which is unsubstituted or substituted with alkyl, alkenyl, alkynyl, halogen, haloalkyl, haloalkenyl, or haloalkynyl; C7-C15 aralkyl which is unsubstituted or substituted with alkyl, alkenyl, alkynyl, halogen, haloalkyl, haloalkenyl, or haloalkynyl; alkoxy; haloalkoxy; carbonyloxy; and halocarbonyloxy; and k is an integer of 1 to 10.

6. The catalyst composition of claim 3, wherein the compound represented by Chemical formula 2 is tris(dibenzylideneacetone)dipalladium(0)_($Pd_2(dba)_3$) or palladium_acetate_($Pd(OAc)_2$).

7. The catalyst composition of claim 3, wherein a molar ratio of the compound represented by Chemical formula 1: the compound represented by Chemical formula 2 is 1:2.

8. A method for preparing a cycloolefin-based polymer comprising polymerizing, in the presence of the catalyst composition of claim 3, a cycloolefin-based monomer represented by Chemical formula 5:

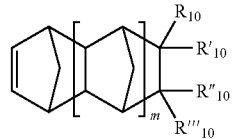

Chemical formula 5 wherein, m is an integer of 0 to 4; and $R_{10}$, $R'_{10}$, $R''_{10}$ and $R'''_{10}$ are the same or different from each other, and are independently selected from the group consisting of hydrogen; halogen; a linear or branched C1-C20 alkyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynyl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; C3-12 cycloalkyl group which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-40 aryl which is unsubstituted or substituted with at least a functional group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a polar functional group including at least an atom selected from the group consisting of oxygen, nitrogen, phosphorus, sulfur, silicon and boron, where, $R_{10}$ and $R'_{10}$, or $R''_{10}$ and $R'''_{10}$ may be linked each other to form C1-C10 alkylidene group, or one of $R_{10}$ and $R'_{10}$ may be linked to one of $R''^{10}$ and $R'''_{10}$ to form a unsaturated or saturated C4-C12 alicylic ring, or a C6-C24 aromatic ring, the polar functional group is selected from the group of —$R_5OR_6$, —$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$—, —$R_5C(=S)SR_6$, —$R_5SO_3R_6$, —$SO_3R_6$, —$R_5N=C=S$, —$N=C=S$, —$NCO$, —$R_5$—$NCO$, —$CN$, —$R_5CN$, —$NNC(=S)R_6$, —

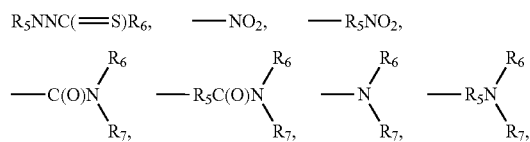

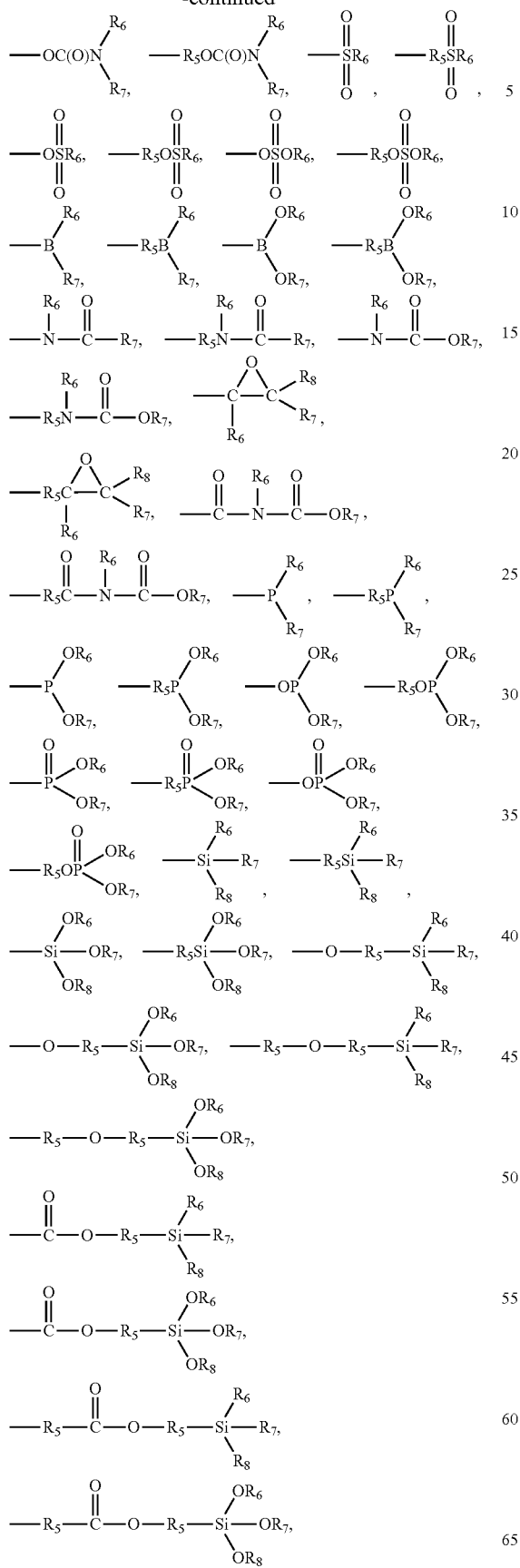
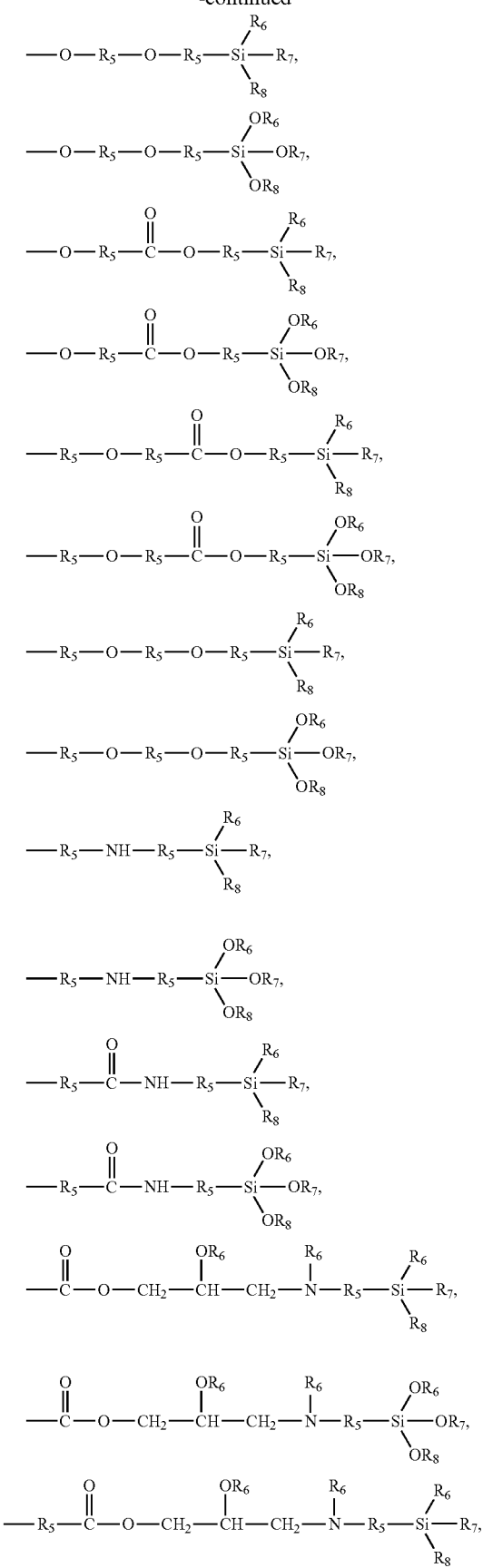

-continued

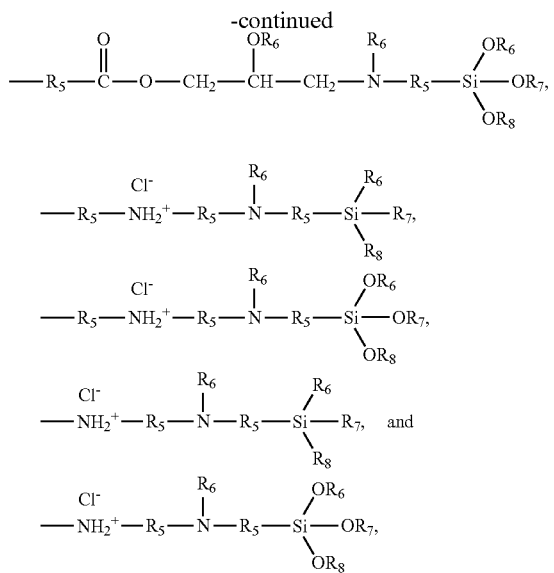

$R_5$ is the same or different from each other and is independently a linear or branched C1-C20 alkylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C3-C12 cycloalkylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-C40 arylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C1 to C20 alkoxylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a C1 to C20 carbonyloxylene which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy, $R_6$, $R_7$ and $R_8$ are the same or different from each other and are independently selected from the group consisting of hydrogen; halogen; a linear or branched C1-C20 alkyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C2-C20 alkenyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a linear or branched C3-C20 alkynyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C3-12 cycloalkyl which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C6-40 aryl group which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; a C1-C20 alkoxy which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy; and a C1-C20 carbonyloxy which is unsubstituted or substituted with at least a functional group selected from the group of halogen, alkyl, alkenyl, alkynyl, haloalkyl, haloalkenyl, haloalkynyl, aryl, haloaryl, aralkyl, haloaralkyl, alkoxy, haloalkoxy, carbonyloxy, halocarbonyloxy, aryloxy, haloaryloxy, silyl and siloxy, and p is an integer of 1 to 10.

9. The method of claim 8, wherein a molar ratio of cycloolefin-based monomer to Group 10 metal is 5,000 to 100,000.

10. The method of claim 8, wherein the cycloolefin-based monomer is polymerized in a solvent selected from the group consisting of dichloromethane, dichloroethane, toluene and chlorobenzene.

11. The method of claim 10, wherein a weight ratio of the solvent to the cycloolefin-based monomer is in the range of 0.5:1 to 5:1.

12. The method of claim 8, wherein the cycloolefin-based polymer is a homopolymer of cycloolefin-based monomer, a two-membered copolymer or three-membered copolymer prepared from cycloolefin-based monomers including polar functional groups that are different from each other, or a two-membered copolymer or three-membered copolymer prepared from a cycloolefin-based monomer including a polar group and a cycloolefin-based monomer not including a polar group.

13. The method of claim 8, wherein the cycloolefin-based polymer has a weight-average molecular weight of 300,000 or higher.

* * * * *